United States Patent
Liu et al.

(10) Patent No.: US 12,430,105 B2
(45) Date of Patent: Sep. 30, 2025

(54) CONVERSION METHOD AND CONVERSION APPARATUS OF TEXT CODES AND GRAPHIC CODES FOR VEHICLE DEVELOPMENT

(71) Applicant: SHANGHAI TOSUN TECHNOLOGY LTD., Shanghai (CN)

(72) Inventors: Chu Liu, Shanghai (CN); Yueyin Xie, Shanghai (CN); Mang Mo, Shanghai (CN)

(73) Assignee: SHANGHAI TOSUN TECHNOLOGY LTD., Shanghai (CN)

( * ) Notice: Subject to any disclaimer, the term of this patent is extended or adjusted under 35 U.S.C. 154(b) by 189 days.

(21) Appl. No.: 18/243,682

(22) Filed: Sep. 8, 2023

(65) Prior Publication Data
US 2024/0403049 A1      Dec. 5, 2024

(30) Foreign Application Priority Data
Jun. 1, 2023   (CN) .......................... 202310640840.3

(51) Int. Cl.
| | | |
|---|---|---|
| G06F 8/34 | (2018.01) | |
| G06F 8/41 | (2018.01) | |
| G06F 8/51 | (2018.01) | |
| G06F 11/3604 | (2025.01) | |

(Continued)

(52) U.S. Cl.
CPC .................. *G06F 8/34* (2013.01); *G06F 8/41* (2013.01); *G06F 8/51* (2013.01); *G06F 11/3604* (2013.01); *G06F 11/3624* (2013.01); *G16B 50/00* (2019.02)

(58) Field of Classification Search
CPC ........ G06F 11/3604; G06F 8/34; G16B 50/00
See application file for complete search history.

(56) References Cited

U.S. PATENT DOCUMENTS

| 7,975,233 B2 | 7/2011 | Macklem et al. |
|---|---|---|
| 2008/0022264 A1 | 1/2008 | Macklem et al. |

(Continued)

FOREIGN PATENT DOCUMENTS

| CN | 106325969 A | 1/2017 |
|---|---|---|
| CN | 109634592 A | 4/2019 |

(Continued)

OTHER PUBLICATIONS

Wei, An-dong, CN 113691403 (translation), Aug. 3, 2021, 13 pgs <CN_113691403.pdf>.*

(Continued)

*Primary Examiner* — Tuan A Vu
(74) *Attorney, Agent, or Firm* — Bayramoglu Law Offices LLC

(57) ABSTRACT

A conversion method and conversion system of text codes and graphic codes for vehicle development. The conversion method of text codes and graphic codes for vehicle development includes: converting the graphic codes into the text codes, and while generating target text codes, inserting configuration information of each execution unit in current graphic codes into an annotation region of the target text codes; and, when converting the target text codes back to graphic codes, extracting the configuration information of the annotation region of the target text codes and loading the configuration information to restore the graphic codes.

15 Claims, 8 Drawing Sheets

S101
The graphic codes are converted into the text codes, and while target text codes are generated, configuration information of each execution unit in current graphic codes is inserted into an annotation region of the target text codes.

S102
when the target text codes are converted back to graphic codes, a graphic program extracts the configuration information of the annotation region of the target text codes and loads the configuration information to restore the graphic codes.

(51) Int. Cl.
  *G06F 11/362*  (2025.01)
  *G16B 50/00*  (2019.01)

(56) References Cited

U.S. PATENT DOCUMENTS

| | | | |
|---|---|---|---|
| 2014/0282177 A1* | 9/2014 | Wang | G16B 50/00 |
| | | | 715/771 |
| 2017/0046481 A1 | 2/2017 | Wang et al. | |
| 2017/0060541 A1 | 3/2017 | Saleh et al. | |
| 2018/0285084 A1* | 10/2018 | Mimlitch, III | G06F 11/3604 |
| 2020/0210152 A1 | 7/2020 | Mimlitch, III et al. | |
| 2021/0342288 A1 | 11/2021 | Das Sharma | |

FOREIGN PATENT DOCUMENTS

| | | |
|---|---|---|
| CN | 110941426 A | 3/2020 |
| CN | 112306481 A | 2/2021 |
| CN | 112947903 A | 6/2021 |
| CN | 113050953 A | 6/2021 |
| CN | 113867719 A | 12/2021 |
| CN | 113961238 A | 1/2022 |
| CN | 114138641 A | 3/2022 |
| CN | 114968345 A | 8/2022 |
| CN | 115202665 A | 10/2022 |
| CN | 115454414 A | 12/2022 |
| CN | 115686478 A | 2/2023 |
| CN | 115718802 A | 2/2023 |
| CN | 115794054 A | 3/2023 |
| CN | 115857905 A | 3/2023 |
| CN | 115934054 A | 4/2023 |
| CN | 116663502 A | 8/2023 |
| JP | H0421005 A | 1/1992 |
| JP | H07261990 A | 10/1995 |
| JP | 2009181446 A | 8/2009 |
| JP | 2011150739 A | 8/2011 |
| JP | 2018081592 A | 5/2018 |
| JP | 2020197867 A | 12/2020 |
| KR | 20130050501 A | 5/2013 |
| RU | 2509662 C2 | 3/2014 |
| RU | 2666238 C2 | 9/2018 |

OTHER PUBLICATIONS

Hong et al., CN 114172793 (translation), Apr. 4, 2023, 25 pgs <CN_114172793.pdf>.*
Reichardt Johannes, DE 199007328 (translation) ,Aug. 31, 2000, 25 pags <DE_19907328.pdf>.*
Dongsheng Li, Research on Techniques of FPGA Parallel Reverse Engineering, A Master Thesis Submitted to University of Electronic Science and Technology of China, 2021, pp. 1-80.
Feng Huizong, et al., Research on Driver Code Quick Generation Technique Based on Real-Time Workshop, Computer Applications and Software, 2016, pp. 226-228, vol. 33 No. 3.
Shen Kai, et al., Simulation Modeling Method under RTX Subsystem Based on Simulink/RTW, Computer Measurement & Control, 2014, pp. 566-568,571, vol. 22 No. 2.

* cited by examiner

S101

The graphic codes are converted into the text codes, and while target text codes are generated, configuration information of each execution unit in current graphic codes is inserted into an annotation region of the target text codes.

S102 when the target text codes are converted back to graphic codes, a graphic program extracts the configuration information of the annotation region of the target text codes and loads the configuration information to restore the graphic codes.

FIG.1

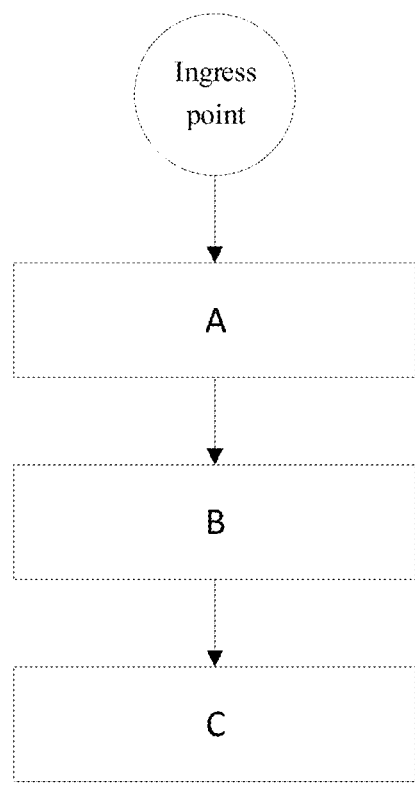

FIG.2 by a computer device, performing operations corresponding to the conversion method of text codes and graphic codes to generate the text codes.  — S201 by a bus adapter, writing compiled execution codes into a debugging device, or, by a burner, writing the compiled execution codes into the debugging device  — S202

CONVERSION METHOD AND CONVERSION APPARATUS OF TEXT CODES AND GRAPHIC CODES FOR VEHICLE DEVELOPMENT

CROSS-REFERENCE TO THE RELATED APPLICATION

This application is based upon and claims priority to Chinese Patent Application No. 202310640840.3 filed on Jun. 1, 2023, the entire content of which is incorporated herein by reference.

TECHNICAL FIELD

The present disclosure relates to the field of vehicular software development technologies, and in particular to a conversion method and conversion system of text codes and graphic codes for vehicle development.

BACKGROUND

During a vehicle development flow, a model is firstly constructed based on graphic codes. But, the graphic codes operate at a computer end and cannot become a carrier for logical operation. For vehicle development, a logic of a vehicle controller must be executed based on text codes. Thus, the graphic codes are to be converted into the text codes before being executed in the vehicle controller.

SUMMARY

The present disclosure relates to a conversion method and conversion system of text codes and graphic codes for vehicle development.

The conversion method includes:
  converting the graphic codes into the text codes, and while generating target text codes, inserting configuration information of each execution unit in current graphic codes into an annotation region of the target text codes; and,
  when converting the target text codes back to graphic codes, extracting, by a graphic program, the configuration information of the annotation region of the target text codes and loading the configuration information to restore the graphic codes.

According to another aspect, the present disclosure further provides a conversion apparatus for text codes and graphic codes, which includes:
  a processor, configured to execute programs of the above conversion method of text codes and graphic codes;
  a storing module, configured to store the programs of performing the above conversion method of text codes and graphic codes; and,
  a displaying module, configured to display a conversion result of the text codes and the graphic codes.

According to a third aspect, the present disclosure further provides a computer readable storage medium, configured to store programs of performing the above conversion method of text codes and graphic codes.

According to a fourth aspect, the present disclosure further provides a processor, configured to execute the programs of the above conversion method of text codes and graphic codes.

According to a fifth aspect, the present disclosure further provides a conversion method of text codes and graphic codes, which is applied to vehicle development. The method includes:

converting vehicle graphic codes into text codes, and while generating target codes, inserting configuration information of each execution unit in current vehicle graphic codes into an annotation region of the target codes; and,
  when converting the target codes back to vehicular graphic codes, extracting the configuration information of the annotation region of the target codes and loading the configuration information to restore vehicular graphic codes.

According to a sixth aspect, the present disclosure further provides an electronic device, including a processor, a readable storage medium, a communication bus and a communication interface, where the processor, the readable storage medium and the communication interface communicate with each other via the communication bus;
  the readable storage medium is configured to store the programs of performing the above conversion method of text codes and graphic codes, and the programs cause the processor to perform operations corresponding to the conversion method of text codes and graphic codes.

According to a seventh aspect, the present disclosure further provides a vehicular development and debugging system, including a computer device, a bus adapter or a burner; where,
  the computer device includes a processor, a readable storage medium, a communication bus and a communication interface; wherein,
  the readable storage medium is configured to store the programs of performing the conversion method of text codes and graphic codes, and the programs cause the processor to perform operations corresponding to the conversion method of text codes and graphic codes so as to generate the text codes;
  the processor, the readable storage medium and the communication interface communicate with the bus adapter via the communication bus;
  the processor is configured to compile at least one fragment of execution codes in the text codes;
  the bus adapter is configured to write the compiled execution code into a debugging device; or,
  the burner is configured to write the compiled executing code into the debugging device.

The contents of the present disclosure aim to provide brief descriptions for the subject described in the specification. Therefore, it should be understood that the above features are merely illustrative and shall not be interpreted as narrowing the scope or essence of the described subject of the specification in any way.

Other features, aspects and advantages of the subject described in the specification will become apparent by way of following specific embodiments, accompanying drawings and claims.

BRIEF DESCRIPTION OF THE DRAWINGS

In order to more clearly describe the technical solutions in the specific embodiments of the present disclosure or the prior arts, the accompanying drawings required for descriptions of the specific embodiments or the prior arts will be briefly introduced.

Apparently, the drawings described hereunder are some embodiments of the present disclosure. Those skilled in the art can obtain other drawings based on these drawings without making creative work.

FIG. 1 is a step diagram illustrating a conversion method of text codes and graphic codes according to some embodiments of the present disclosure.

FIG. 2 illustrates one graphic code case involved in some embodiments of the present disclosure.

DETAILED DESCRIPTION OF THE EMBODIMENTS

Figure 3:
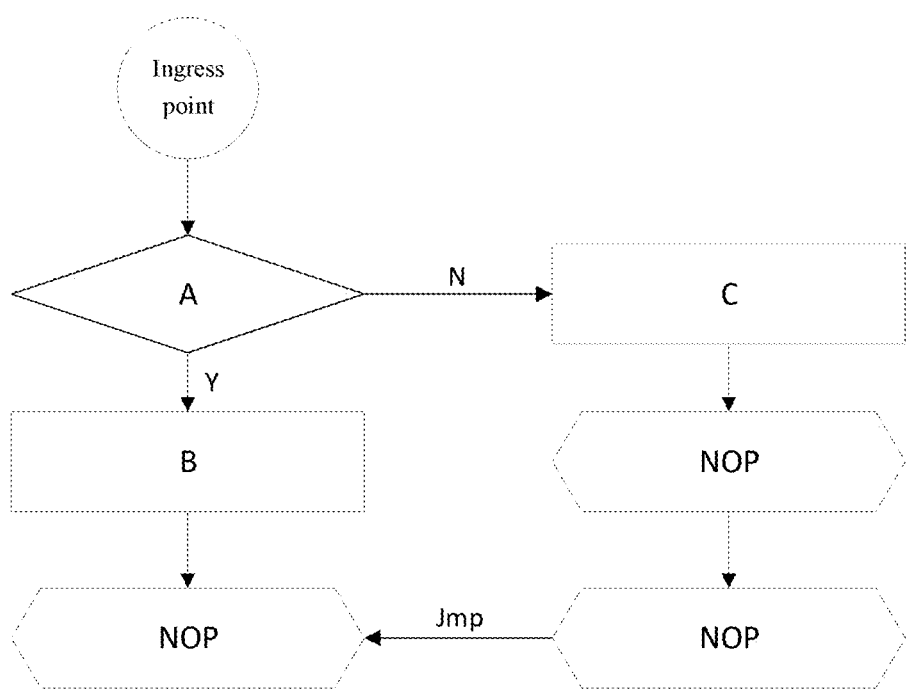
FIG. 3 illustrates another graphic code case involved in some embodiments of the present disclosure.

In order to make the object, technical solutions and advantages of the present disclosure clearer, the technical solutions of the present disclosure will be fully and clearly described in combination with the drawings below. Apparently, the embodiments described herein are some of the embodiments of the present disclosure rather than all embodiments. All other embodiments obtained by those skilled in the art based on these embodiments in the present disclosure without making creative work shall fall within the scope of protection of the present disclosure.

The inventor has known that during a vehicle development process, it is desired to rely on a version management software such as an open-source distributed version control system (Git) to perform management, for example, on text-based C codes. However, these management softwares have difficulty in managing graphic codes and comparing a difference between graphic code versions. Thus, a file used to compare the difference in the version management system is usually text codes. When a user browses a difference item between different versions of text codes, it is very difficult to reversely derive the implementation details of the graphic codes from the specific difference codes. Furthermore, if the text codes have logical problem, difference comparison is to be performed from the text codes corresponding to the program version subjected to the problem, and the graphic codes are derived reversely for correction, and then the corrected graphic codes are converted again into the text codes such that the text codes generated from the graphic codes are executed in the vehicle controller. Then, the text codes are converted again back into the graphic codes for correction, and then the process of continuously generating the text codes from the graphic codes will be repeated until the programs are correct.

Further, because the same or similar kinds of software programs in the vehicle development process can only perform one-way generation between graphic codes and C codes and cannot ensure the execution actions in the graphic codes and the C codes are in strict one-to-one correspondence, namely, the C codes are generated from the graphic codes, and then the graphic codes are generated again from the C codes and at this time, there may be a difference between the original graphic codes and the re-generated graphic codes.

The cause for the difference between the original graphic codes and the re-generated graphic codes is described through one case below.

Generally, one action is repeated in the graphic codes by simply setting a repetition number of the action, for example, if the action k=k+1 is to be cycled three times, the repetition number of the action k=k+1 is set to 3, and but based on the C codes generated from the graphic codes, there will be multiple results in combination with different use scenarios:

(1) Under a general cyclic logic, i.e. a general scenario, the C codes are generated as follows:

```
for (i=0; i<3; i++){
    k = k + 1;
}
```

(2) In a scenario of high performance requirement, the C codes are generated as follows:

$$k = k + 1;$$
$$k = k + 1;$$
$$k = k + 1;$$

Different C codes are generated in the above two scenarios. If the different C codes are converted back into the graphic codes again, different results will generated, namely, three actions instead of one may occur in the graphic codes converted back, or the graphic codes use rhombus branch to achieve the for syntax rather than simply use the repetition attribute.

As a result, the conversion method of text codes and graphic codes for vehicle development in at least one embodiment of the present disclosure includes: converting the graphic codes into the text codes, and while generating target text codes, inserting configuration information of each execution unit in current graphic codes into an annotation region of the target text codes; and, when converting the target text codes back to graphic codes, extracting, by a graphic program, the configuration information of the annotation region of the target text codes and loading the configuration information so as to obtain the configuration information of each execution unit in the graphic codes, and then based on the configuration information, restoring the graphic codes.

The configuration information in some embodiments is the graphic codes themselves, i.e. the information after persistence of the graphic codes is referred to as the configuration information. The graphic codes are presented in the form of block diagram, and contain programs such as sequence execution, branch jump execution and cyclic execution and the like.

Each time the graphic codes are converted into the text codes, the configuration information of the graphic codes is inserted as an annotation into the annotation region of the target text codes. Thus, it is guaranteed that when the text codes are converted back into the graphic codes, the graphic codes can be exactly identical to the original graphic codes. Therefore, multiple conversions can be repeated while the graphic codes are in one-to-one correspondence with the text codes.

Various non-limiting implementations of the embodiments of the present disclosure will be described below in combination with the drawings.

As shown in FIG. 1, one or more embodiments provide a conversion method of text codes and graphic codes, which includes the following steps.

At step S101, the graphic codes are converted into the text codes, and while target text codes are generated, configuration information of each execution unit in current graphic codes is inserted into an annotation region of the target text codes.

At step S102, when the target text codes are converted back to graphic codes, a graphic program extracts the configuration information of the annotation region of the target text codes and loads the configuration information to obtain the configuration information of each execution unit in the graphic codes and then based on the configuration information, restores the graphic codes.

In some embodiments, the configuration information is inserted in the form of text into the annotation region of the target text codes after being subjected to serialization encoding; and when the target text codes are converted back to the graphic codes, the graphic program extracts configuration information text of the annotation region for deserialization decoding and loads the configuration information to restore the graphic codes.

Specifically, the graphic program involved in some embodiments refers to a program which operates on a personal computer (PC) and presents, in the form of computer graphics, the structures such as sequence execution, branch jump execution and cyclic execution and the like.

In some embodiments, the serialization encoding manner, for example, includes but not limited to a base64 encoding manner; if the base64 encoding manner is adopted, the corresponding deserialization decoding manner is a base64 decoding manner.

It is to be noted that descriptions will be made to the following cases, with the base64 encoding manner and the base64 decoding manner as an example.

In some embodiments, the text codes include but not limited to C codes, Java codes, Python Codes, Pascal codes, C++ codes, Visual Basic codes and C# codes and the like.

It is noted that in the following cases, descriptions are made with the conversion between the graphic codes and the C codes as an example, and the parentheses of the function call statements in the C codes may be void or non-void, for example, when there is a parameter, is non-void. In some embodiments, for ease of descriptions, the function call statements without parameters are used.

In some embodiments, the type of each execution unit in the graphic codes may be preset, for example, the execution units in the graphic codes are preset to a sequence execution unit, a branch jump unit, a nested execution unit, and a cyclic unit. The type of each execution unit can be identified by reading the type attribute of the execution unit through the graphic codes. Different types of execution units can be converted into the C codes in the following methods:

the sequence execution units in the graphic codes are directly converted into the C codes corresponding to unit action;

the branch jump units in the graphic codes are converted into the C codes of "if" or "else if" or "else" structure;

the nested execution units in the graphic codes are converted into one function executing nested C codes and one function-called C code; and the cyclic units in the graphic codes are converted into one tag, one goto statement and the C codes corresponding to the action of the cyclic units.

In an implementation of converting the graphic codes into the C codes, it is assumed that the graphic codes containing the sequence execution units as shown in FIG. 2 are taken as an example.

Specifically, when the graphic codes are converted into the C codes, the execution units are sequentially converted based on an execution order, and the corresponding C codes are as follows:

A( );
B( );
C( );

In another implementation of converting the graphic codes into the C codes, it is assumed that the graphic codes containing the branch jump execution units as shown in FIG. 3 are taken as an example.

When the graphic codes are converted into the C codes, two branches are to be set for a return value of the A. When the return value of the A is logic true, a first branch, i.e. B, is executed; after B is executed, the logic continues execution downward and otherwise, a second branch, i.e. C, is executed; after C is executed, the logic jumps to a next command of the B to continue execution. The corresponding C codes are as follows:

```
if (A( )){
  B( );
} else {
  C( );
}
```

Figure 4:
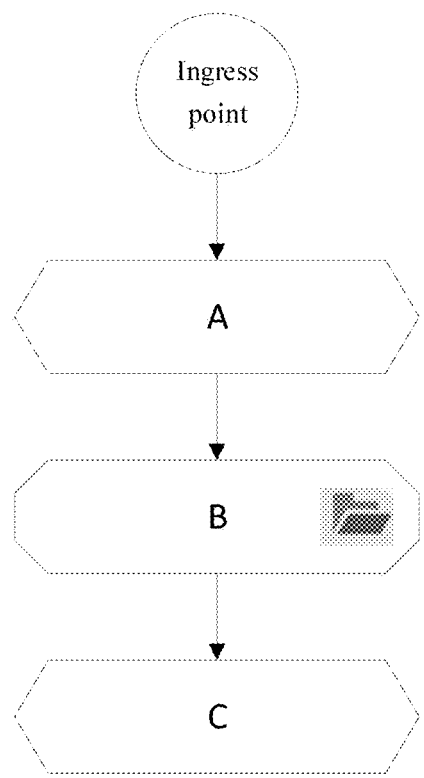
FIG. 4 illustrates a third graphic code case involved in some embodiments of the present disclosure.

In a third implementation of converting the graphic codes into the C codes, it is assumed that that the graphic codes containing the nested execution units as shown in FIG. 4 are taken as an example.

Figure 5:
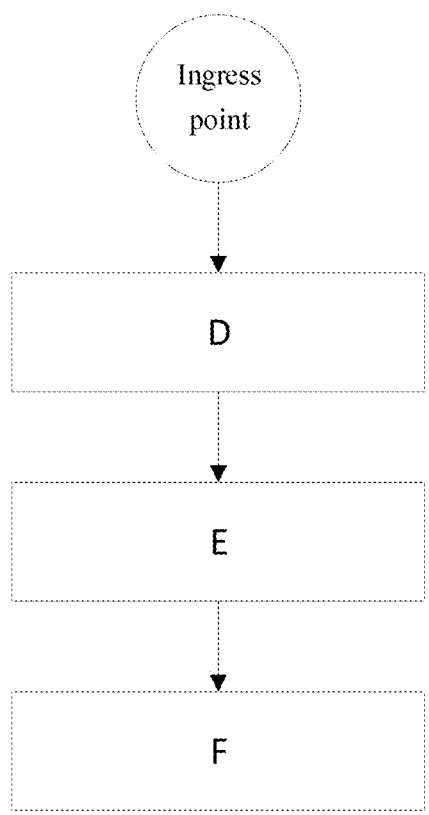
FIG. 5 illustrates a sub-graphic code of an execution unit B in the third graphic code case involved in some embodiments of the present disclosure.

As shown in FIG. 5, the execution unit B in the graphic codes is a nested execution unit in which are sub-graphic codes.

When the graphic codes are converted into the C codes, it is required to firstly convert the contents of the execution unit B into one C code function, and the nested inner C codes are as follows:

```
int B(void){
  D( );
```

```
    E( );
    F( );
}
```

Thus, the code generation of the execution unit B becomes call of the function B and the nested outer C codes are as follows:

```
A( );
B( );
C( );
```

Figure 6:
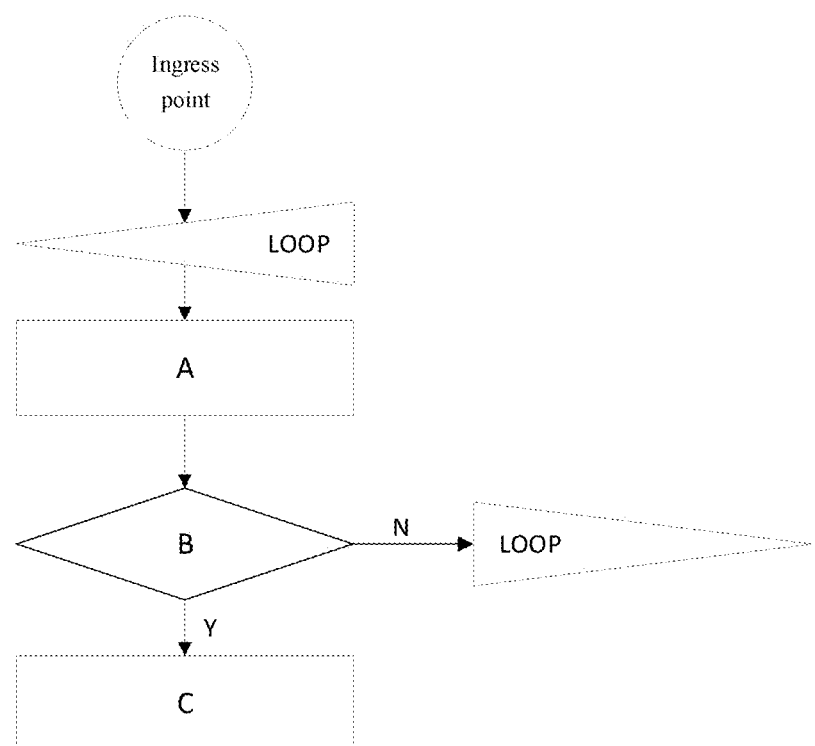
FIG. 6 illustrates a fourth graphic code case involved in some embodiments of the present disclosure.

In a fourth implementation of converting the graphic codes into the C codes, it is assumed that that the graphic codes containing the cyclic execution units as shown in FIG. 6 are taken as an example.

After the execution unit A is completed, the execution of the execution unit B is started. It is a determination. When the return result is logical true, the execution unit C is executed downward, and otherwise, rightward jump is performed with the skip tag being "Loop". It means that the program will jump to above the execution unit A to continue downward execution, and the execution unit A and the execution unit B form one cycle.

When the graphic codes are converted into the C codes, a tag Loop is to be set above the execution unit A, and when the execution unit B returns logic false, the goto statement of the C code language is used to jump to the tag and the generated C codes are as follows:

```
Loop:
A( );
if (B( )){
   goto Loop;
}
C( );
```

In some embodiments, the method of inserting the configuration information into the annotation region of the target codes includes: generating persistent configuration information of the graphic codes; and, inserting the persistent configuration information in the form of text into the annotation region of the target codes after being subjected to serialization encoding.

Specifically, the one-to-one correspondence of the graphic codes and the codes may be achieved by performing encoding and decoding through character string or file.

For example, the generated persistent configuration information of the graphic codes is as follows:
conf=5704664608865866268;1;−1;
4143886487092279683;−1;0;0;0;0;yOu/2rXj;;−1;0

After the persistent configuration information undergoes base64 encoding, the following character string s can be obtained:

Y29uZj01NzA0NjY0NjA4ODY1ODY2MjY4OzE7LTE7NDE0Mzg4NjQ4NzA5MjI3O
TY4MzstMTswOzA7MDswO3lPdS8yclhqOzstMTsw By simply inserting the character string s into the annotation region of the target C codes in the form of text, all information of the graphic codes can be stored in the C codes. When the C codes are to be converted back into the graphic codes, it is only required to extract the character string s from the C codes and perform base64 decoding operation on the character string s to obtain the persistent configuration information of the graphic codes, and load the persistent configuration information to obtain the complete graphic codes.

In some embodiments, when the graphic codes are converted into the C codes, in addition to displaying, in the target C codes, the configuration information of each execution unit in the current graphic codes, positioning information of each execution unit in the current graphic codes is also displayed in the target C codes.

Specifically, the positioning information includes global unique ids in one-to-one correspondence with the execution units in the graphic codes. Each global unique id is generated by calling system API function coCreateGuid. By using the global unique id, the execution unit can be directly positioned, so as to achieve the conversion from the graphic codes to the text codes: each text code line corresponding to the graphic codes can be directly positioned by using the global unique id; and the conversion from the text codes to the graphic codes: the execution unit corresponding to the text code line can be directly positioned by using the global unique id.

In an optional implementation of displaying the positioning information in the target C codes, the graphic codes are converted into the C codes and while the target C codes are generated, the positioning information of each execution unit in the current graphic codes is inserted into the corresponding target C code line.

By use of the positioning information, a position of an execution unit in the graphic codes corresponding to a code line in the C codes can be determined so as to, in an application scenario of checking the logic of the C codes, greatly improve the checking convenience and efficiency; and further, by use of the positioning information, a position of a corresponding code line in the C codes corresponding to an execution unit in the graphic codes can be determined, so as to, in an application scenario of performing further test on the function and the like in the C codes, greatly increase the test efficiency.

The method of inserting the positioning information into the corresponding target C code lines will be detailed below in combination with specific cases.

Figure 7:
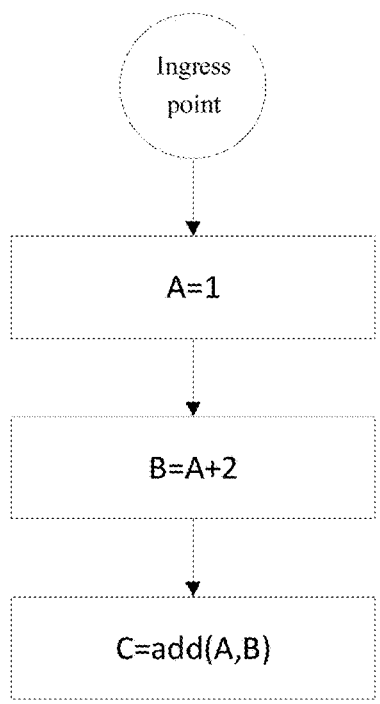
FIG. 7 illustrates a fifth graphic code case involved in some embodiments of the present disclosure.
Figure 8:
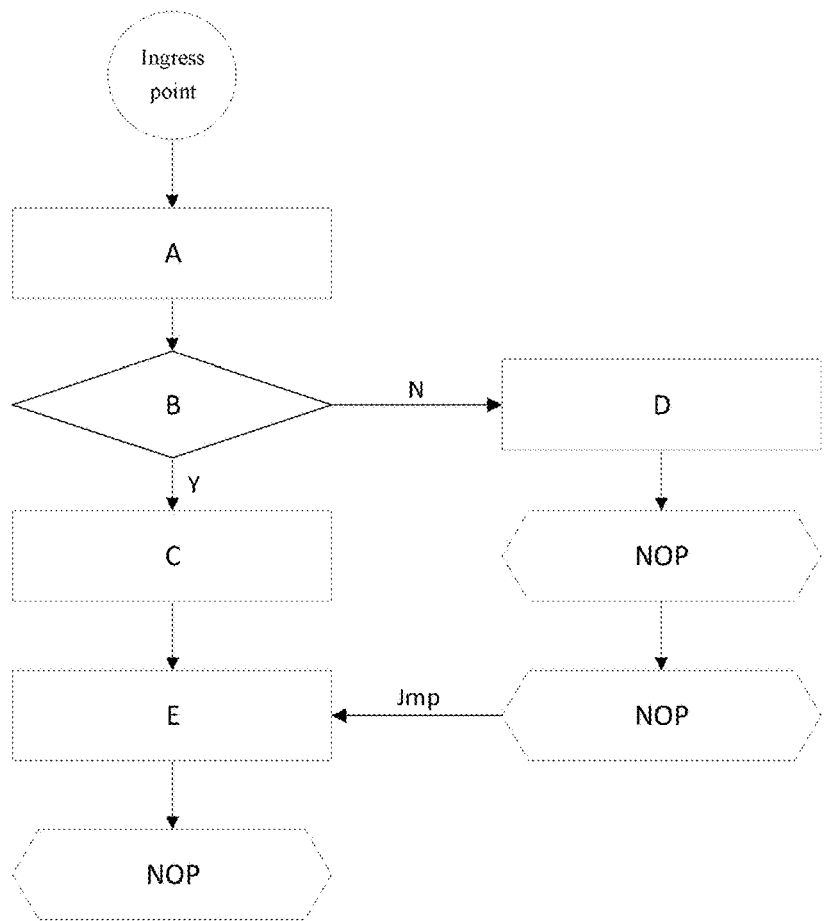
FIG. 8 illustrates a sixth graphic code case involved in some embodiments of the present disclosure.

It is assumed that the graphic codes shown in FIG. 7 are taken as an example:

At step S201, when the graphic codes are converted into the C codes, the corresponding global unique id is generated for each of the execution units A, B and C. The correspondence between the execution units and the ids is indicated in the Table below.

| Execution unit | id |
| --- | --- |
| A = 1; | 796586134100579186 |
| B = A + 2; | 4477997354382728721 |
| C = add(A, B); | 623479023297457637 |

At step S202, based on a conversion rule, the C codes are generated line by line from the graphic codes, and the correspondence of line numbers, C codes and ids is recorded in the Table below:

| Line number | C codes | id |
|---|---|---|
| 1 | A = 1; | 796586134100579186 |
| 2 | B = A + 2; | 4477997354382728721 |
| 3 | C = add(A, B); | 623479023297457637 |

At step S203, the id is added as positioning information into the corresponding target code line in the form of annotation, and preferably into the right of the corresponding target code line, and thus the generated target C codes are as follows:

| | |
|---|---|
| A = 1; | // 796586134100579186 |
| B = A + 2; | // 4477997354382728721 |
| C = add(A, B); | // 623479023297457637 |

In another optional implementation of displaying the positioning information in the target codes, when the graphic codes are converted into the codes, one temporary file is established to temporarily store the positioning information of each execution unit in the current graphic codes; and the positioning information, after being subjected to serialization encoding, is inserted into the annotation region of the target codes in the form of text; where the positioning information is an association file between each execution unit and the corresponding target code line.

The method of displaying the positioning information in the form of temporary file in the annotation region of the target C codes is detailed below in combination with specific cases.

It is still assumed that the graphic codes shown in FIG. 7 are taken as an example.

At step S301, when the graphic codes are converted into the C codes, the corresponding global unique id is generated for each of the execution units A, B and C. The correspondence between the execution units and the ids is indicated in the Table below.

| Execution unit | id |
|---|---|
| A = 1 | 796586134100579186 |
| B = A + 2 | 4477997354382728721 |
| C = add(A, B) | 623479023297457637 |

At step S302, based on a conversion rule, the C codes are generated line by line from the graphic codes, and the correspondence of line numbers, C codes and ids is recorded in the Table below:

| Line number | C codes | id |
|---|---|---|
| 1 | A = 1; | 796586134100579186 |
| 2 | B = A + 2; | 4477997354382728721 |
| 3 | C = add(A, B); | 623479023297457637 |

After the C codes are generated, an association file in which the code line numbers correspond to the ids is obtained, where there are a total of three lines, which are indicated below:

| Line number | id |
|---|---|
| 1 | 796586134100579186 |
| 2 | 4477997354382728721 |
| 3 | 623479023297457637 |

At step S303, the graphic codes take the association file of the code line numbers and the ids as the positioning information and obtain a character string s1 through base64 encoding as follows:

Nzk2NTg2MTM0MTAwNTc5MTg2DQo0NDc3OTk3MzU0MzgyNzI4NzIxDQo2MjM0NzkwMjMyOTc0NTc2Mzc

At step S304, the encoded character string s1 is inserted in the form of text into the annotation region of the target C codes. The target C codes have the following contents:

```
A = 1;
B = A + 2;
C = add(A, B);
//Nzk2NTg2MTM0MTAwNTc5MTg2DQo0NDc3OTk3MzU0MzgyNzI4NzIxDQo2MjM0NzkwMjMyOTc0NTc2Mzc
```

The conversion method of the C codes and the graphic codes in the present embodiments of the present disclosure will be detailed below in combination with specific complete cases which specifically involve the full steps of the conversion from the graphic codes to the C codes and of the conversion from the C codes back to the graphic codes.

Case 1 (the Positioning Information is Inserted into the Right of the Corresponding Target C Code Line)

It is assumed that the graphic codes in this example are as shown in FIG. 7.

According to the method described in some embodiments, the steps for performing mutual conversion between the graphic codes and the C codes are as follows:

At step S401, a corresponding global unique id is generated for each of the execution units A, B and C, and the correspondence of the execution units and the ids is indicated in the Table below:

| Execution unit | id |
| --- | --- |
| A = 1 | 796586134100579186 |
| B = A + 2 | 4477997354382728721 |
| C = add(A, B) | 623479023297457637 |

At step S402, based on a conversion rule, the C codes are generated line by line from the graphic codes, and the correspondence of line numbers, C codes and ids is recorded in the Table below:

| Line number | C codes | id |
| --- | --- | --- |
| 1 | A = 1; | 796586134100579186 |
| 2 | B = A + 2; | 4477997354382728721 |
| 3 | C = add(A, B); | 623479023297457637 |

After the codes are generated, a target C code file including a total of three lines is obtained, which is indicated in the Table below:

| Line number | Codes |
| --- | --- |
| 1 | A = 1; |
| 2 | B = A + 2; |
| 3 | C = add(A, B); |

After the codes are generated, a file in which the code line numbers correspond to the ids is obtained, where there are a total of three lines, which are indicated below:

| Line number | id |
| --- | --- |
| 1 | 796586134100579186 |
| 2 | 4477997354382728721 |
| 3 | 623479023297457637 |

At step S403, the ids as the positioning information are added in the form of annotation to the right of the corresponding target code lines, and the generated target C codes have the following contents:

| | |
| --- | --- |
| A = 1; | // 796586134100579186 |
| B = A + 2; | // 4477997354382728721 |
| C = add(A, B); | // 623479023297457637 |

At step S404, the graphic codes enable the persistent configuration information of each execution unit to go through base64 encoding.

It is assumed that the persistent configuration information is as follows:

```
[ao]
conf=5864543089582057106;1;-1;796586134100579186;-1;0;0;0;0;yOu/2rXj;;-1;0
[a0]
conf=623479023297457637;0;4477997354382728721;-1;-1;0;1;0;0;QyA9IEI_;;0;0
[a1]
conf=4477997354382728721;0;796586134100579186;623479023297457637;-1;0;3;0;0;
QiA9IEEgKyAy;;0;0
[a2]
conf=796586134100579186;0;5864543089582057106;4477997354382728721;-1;0;1;0;
0;QSA9IDE_;;0;0
```

Then, a character string s2 can be obtained through base64 encoding, where the character string has the following contents:

```
W2FvXQ0KY29uZj01ODY0NTQzMDg5NTgyMDU3MTA2OzE7LTE7Nzk2NTg2MT
M0MTAwNTc5MTg2Oy0xOzA7MDswOzA7eU91LzJyWGo7Oy0xOzANClthMF0NCmNv
bmY9NjIzNDc5MDIzMjk3NDU3NjM3OzA7NDQ3Nzk5NzM1NDM4MjcyODcyMTstMTst
MTswOzE7MDswO1F5QTlJRUlfOzswOzANClthMV0NCmNvbmY9NDQ3Nzk5NzM1ND
M4MjcyODcyMTswOzc5NjU4NjEzNDEwMDU3OTE4Njs2MjM0Nzkwc MjMyOTc0NTc2M
zc7LTE7MDszOzA7MDtRaUE5SUVFZ0t5QXk7OzA7MA0KW2EyXQ0KY29uZj03OTY1
ODYxMzQxMDA1NzkxODY7MDs1ODY0NTQzMDg5NTgyMDU3MTA2OzQ0Nzc5OTc
zNTQzODI3Mjg3MjE7LTE7MDsxOzA7MDtRU0E5SURFXzs7MDsw
```

At step S405, the graphic codes insert the encoded character string s2 as an annotation in the form of text into the annotation region of the target C codes. The complete target C codes after conversion are as follows:

```
A= 1;             // 796586134100579186
B=A + 2;          // 4477997354382728721
C= add(A, B);     // 623479023297457637
//W2FvXQ0KY29uZj01ODY0NTQzMDg5NTgyMDU3MTA2OzE7LTE7Nzk2NTg
2MTM0MTAwNTc5MTg2Oy0xOzA7MDswOzA7eU91LzJyWGo7Oy0xOzANClthMF0NC
mNvbmY9NjIzNDc5MDIzMjk3NDU3NjM3OzA7NDQ3Nzk5NzM1NDM4MjcyODcyMTst
```

-continued

MTstMTswOzE7MDswO1F5QTlJRUlfOzswOzANClthMV0NCmNvbmY9NDQ3Nzk5NzM
1NDM4MjcyODcyMTswOzc5NjU4NjEzNDEwMDU3OTE4Njs2MjM0NzkwMjMyOTc0N
Tc2Mzc7LTE7MDszOzA7MDtRaUE5SUVFZ0t5QXk7OzA7MA0KW2EyXQ0KY29uZj03
OTY1ODYxMzQxMDA1NzkxODY7MDs1ODY0NTQzMDg5NTgyMDU3MTA2OzQ0Nzc
5OTczNTQzODI3Mjg3MjE7LTE7MDsxOzA7MDtRU0E5SURFXzs7MDsw At step S406, the conversion of the graphic codes and the C codes is completed.

At step S407, when the C codes are to be converted back to the graphic codes, the positioning information and the persistent configuration information of the graphic codes are obtained by reading the id information at the right of each code line in the C code file and the annotation information of the annotation region, and then the graphic codes load the persistent configuration information to restore the graphic codes corresponding to the C codes one to one.

Case 2 (the Positioning Information is Inserted in the Form of Text into the Annotation Region of the Target C Codes)

It is assumed that the graphic codes in the embodiment are as shown in FIG. 8.

The graphic codes have five execution units: A, B, C, D and E. During program execution, A is firstly executed, and then B is executed. Based on the result of the B, subsequent steps are performed. When the return value of the B is logical true, C is executed and otherwise, D is executed. After the C is executed, E is executed. After the D is executed, E is executed, without executing NOP. After the E is executed, the program is ended without executing NOP.

According to the method described in some embodiments, the steps for performing mutual conversion of the graphic codes and the C codes are as follows:

At step S501, the corresponding global unique id is generated for each of the execution units A, B, C, D and E, where the id is a 64-bit integer. Different execution units correspond to different ids, and the correspondence between the execution units and the ids is indicated in the Table below:

| Execution unit | id |
|---|---|
| A | 4143886487092279683 |
| B | 140467269321627285 |
| C | 6482379969619643549 |
| D | 3303683057652484263 |
| E | 3598387971060086837 |

At step S502, based on a rule, the C codes are generated line by line from the graphic codes. During the generation process, for the execution unit in the C codes generated at each line, the graphic codes record the correspondence of the line numbers, the C codes and the ids, where there is no execution unit information in the fourth and sixth lines, and thus no id is recorded. The correspondence of the line numbers, the C codes and the ids in the embodiment is indicated in the Table below:

| Line number | C codes | id |
|---|---|---|
| 1 | A( ); | 4143886487092279683 |
| 2 | if (B( )){ | 140467269321627285 |
| 3 | C( ); | 6482379969619643549 |
| 4 | } else { | empty |
| 5 | D( ); | 3303683057652484263 |
| 6 | } | empty |
| 7 | E( ); | 3598387971060086837 |

After the C codes are generated, a target C code file including a total of 7 lines is obtained, which is indicated in the Table below:

| Line number | Codes |
|---|---|
| 1 | A( ); |
| 2 | if (B( )){ |
| 3 | C( ); |
| 4 | } else { |
| 5 | D( ); |
| 6 | } |
| 7 | E( ); |

After the C codes are generated, an association file in which the code line numbers correspond to the ids is obtained, where there are a total of 7 lines, which are indicated below:

| Line number | id |
|---|---|
| 1 | 4143886487092279683 |
| 2 | 140467269321627285 |
| 3 | 6482379969619643549 |
| 4 | / |
| 5 | 3303683057652484263 |
| 6 | / |
| 7 | 3598387971060086837 |

At step S503, the graphic codes obtain a character string s3 by performing base64 encoding on the association file of the code line numbers and the ids, where the character string has the following contents:

NDE0Mzg4NjQ4NzA5MjI3OTY4Mw0KMTQwNDY3MjY5MzIxNjI3Mjg1DQo2
NDgyMzc5OTY5NjE5NjQzNTQ5DQoNCjMzMDM2ODMwNTc2NTI0ODQyNjMNCg0K
MzU5ODM4Nzk3MTA2MDA4NjgzNw At step S504, the graphic codes enable the persistent configuration information of each execution unit to go through base64 encoding.

It is assumed that the persistent configuration information is as follows:

```
[ao]
  conf=5704664608865866268;1;-1;4143886487092279683;-1;0;0;0;0;yOu/2rXj;;-1;0
[a0]
  conf=140467269321627285;0;4143886487092279683;6482379969619643549;3303683
057652484263;0;0;0;0;Qg_;;0;0
[a1]
  conf=6482379969619643549;0;140467269321627285;3598387971060086837;-1;0;1;
0;Qw_;;0;0
[a2]
  conf=3303683057652484263;0;140467269321627285;8309716131964563539;-1;0;1;
0;RA_;;0;0
[a3]
  conf=4182729410035600018;0;8309716131964563539;-1;-1;0;0;0;0;Tk9Q;;-1;0
[a4]
  conf=3598387971060086837;0;6482379969619643549;3450332134183460644;-1;0;1;
0;0;RQ_;;0;0
[a5]
  conf=8309716131964563539;0;3303683057652484263;4182729410035600018;-1;0;0;
0;0;Tk9Q;;-1;0
[a6]
  conf=3450332134183460644;0;3598387971060086837;-1;-1;0;0;0;0;Tk9Q;;-1;0
[a7]
  conf=4143886487092279683;0;5704664608865866268;140467269321627285;-1;0;1;
0;QQ_;;0;0;
``` thus, a character string s4 is obtained through base64 encoding, where the character string is indicated below:

```
W2FvXQ0KY29uZj01NzA0NjY0NjA4ODY1ODY2MjY4OzE7LTE7NDE0Mzg4NjQ
4NzA5MjI3OTY4MzstMTswOzA7MDswO3lPdS8yclhqOzstMTswDQpbYTBdDQpjb25mP
TE0MDQ2NzI2OTMyMTYyNzI4NTswOzQxNDM4ODY0ODcwOTIyNzk2ODM7NjQ4Mj
M3OTk2OTYxOTY0MzU0OTszMzAzNjgzMDU3NjUyNDg0MjYzOzA7MDswOzA7UWd
fXzs7MDswDQpbYTFdDQpjb25mPTY0ODIzNzk5Njk2MTk2NDM1NDk7MDsxNDA0Nj
cyNjkzMjE2MjcyODU7MzU5ODM4Nzk3MTA2MDA4NjgzNzstMTswOzE7MDswO1F3X
187OzA7MA0KW2EyXQ0KY29uZj0zMzAzNjgzMDU3NjUyNDg0MjYzOzA7MTQwND
Y3MjY5MzIxNjI3Mjg1OzgzMDk3MTYxMzE5NjQ1NjM1Mzk7LTE7MDsxOzA7MDtSQ
V9fOzswOzANClthM10NCmNvbmY9NDE4MjcyOTQxMDAzNTYwMDAxODswOzgzM
Dk3MTYxMzE5NjQ1NjM1Mzk7LTE7LTE7MDswOzA7MDtUazlROzstMTswDQpbYTRd
DQpjb25mPTM1OTgzODc5NzEwNjAwODY4Mzc7MDs2NDgyMzc5OTY5NjE5NjQzNT
Q5OzM0NTAzMzIxMzQxODM0NjA2NDQ7LTE7MDsxOzA7MDtSUV9fOzswOzANClth
NV0NCmNvbmY9ODMwOTcxNjEzMTk2NDU2MzUzOTswOzMzMDM2ODMwNTc2NT
I0ODQyNjM7NDE4MjcyOTQxMDAzNTYwMDAxODstMTswOzA7MDswO1RrOVE7Oy
0xOzANClthNl0NCmNvbmY9MzQ1MDMzMjEzNDE4MzQ2MDY0NDswOzM1OTgzOD
c5NzEwNjAwODY4Mzc7LTE7LTE7MDswOzA7MDtUazlROzstMTswDQpbYTddDQpjb2
5mPTQxNDM4ODY0ODcwOTIyNzk2ODM7MDs1NzA0NjY0NjA4ODY1ODY2MjY4Oz
E0MDQ2NzI2OTMyMTYyNzI4NTstMTswOzE7MDswO1FRX187OzA7MA0K
```

At step S505, the graphic codes add the character strings s3 and s4 as annotations in the form of text, i.e. "//s1,s2" to the annotation region of the target C codes. The generated complete target C codes are as indicated below:

```
A( );
if (B( )){
  C( );
} else {
  D( );
}
E( );
//NDE0Mzg4NjQ4NzA5MjI3OTY4Mw0KMTQwNDY3MjY5MzIxNjI3Mjg1DQo2ND
gyMzc5OTY5NjE5NjQzNTQ5DQoNCjMzMDM20DMwNTc2NTI0ODQyNjMNCg0KMz
U5ODM4Nzk3MTA2MDA4NjgzNw,
W2FvXQ0KY29uZj01NzA0NjY0NjA4ODY1ODY2MjY4OzE7LTE7NDE0Mzg4NjQ4NzA
5MjI3OTY4MzstMTswOzA7MDswO3lPdS8yclhqOzstMTswDQpbYTBdDQpjb25mPTE0M
DQ2NzI2OTMyMTYyNzI4NTswOzQxNDM4ODY0ODcwOTIyNzk2ODM7NjQ4MjM3OT
k2OTYxOTY0MzU0OTszMzAzNjgzMDU3NjUyNDg0MjYzOzA7MDswOzA7UWdfXzs7
MDswDQpbYTFdDQpjb25mPTY0ODIzNzk5Njk2MTk2NDM1NDk7MDsxNDA0NjcyNjk
zMjE2MjcyODU7MzU5ODM4Nzk3MTA2MDA4NjgzNzstMTswOzE7MDswO1F3X187Oz
A7MA0KW2EyXQ0KY29uZj0zMzAzNjgzMDU3NjUyNDg0MjYzOzA7MTQwNDY3MjY
```

-continued

```
5MzIxNjI3Mjg1OzgzMDk3MTYxMzE5NjQ1NjM1Mzk7LTE7MDsxOzA7MDtSQV9fOzs
wOzANClthM10NCmNvbmY9NDE4MjcyOTQxMDAzNTYwMDAxODswOzgzMDk3MT
YxMzE5NjQ1NjM1Mzk7LTE7LTE7MDswOzA7MDtUazlROzstMTswDQpbYTRdDQpjb2
5mPTM1OTgzODc5NzEwNjAwODY4Mzc7MDs2NDgyMzc5OTY5NjE5NjQzNTQ5OzM0
NTAzMzIxMzQxODM0NjA2NDQ7LTE7MDsxOzA7MDtSUV9fOzswOzANClthNV0NCm
NvbmY9ODMwOTcxNjEzMTk2NDU2MzUzOTswOzMzMDM2ODMwNTc2NTI0ODQyN
jM7NDE4MjcyOTQxMDAzNTYwMDAxODstMTswOzA7MDswO1RrOVE7Oy0xOzANCl
thNl0NCmNvbmY9MzQ1MDMzMjEzNDE4MzQ2MDYONDswOzM1OTgzODc5NzEwNj
AwODY4Mzc7LTE7LTE7MDswOzA7MDtUazlROzstMTswDQpbYTddDQpjb25mPTQxN
DM4ODY0ODcwOTIyNzk2ODM7MDs1NzA0NjY0NjA4ODY1ODY2MjY4OzE0MDQ2N
zI2OTMyMTYyNzI4NTstMTswOzE7MDswO1FRX187OzA7MA0K
```

At step S506, the conversion from the graphic codes to the C codes is completed.

At step S507, when the C codes are converted back to the graphic codes, the annotation information of the annotation region of the target C codes is firstly extracted to obtain two character strings s5 and s6 separated by comma, where the character string s5 is the base64-encoded positioning information, and the character string s6 is the base64-encoded persistent configuration information of the graphic codes. The graphic codes load the persistent configuration information to obtain the graphic codes corresponding to the C codes one to one.

In conclusion, in the conversion method of codes and graphic codes in some embodiments, each time the graphic codes are converted into the C codes, the configuration information of the graphic codes is inserted as an annotation into the annotation region of the target codes so as to ensure the graphic codes can be exactly identical to the original graphic codes when the C codes are converted again back into the graphic codes. In this way, multiple conversions can be repeated while the graphic codes are always in one-to-one correspondence with the C codes. Furthermore, in some embodiments of the present disclosure, by use of the positioning information, a position of an execution unit in the graphic codes corresponding to a code line in the C codes can be determined so as to, in an application scenario of checking the logic of the C codes, greatly improve the checking convenience and efficiency; and further, by use of the positioning information, a position of a corresponding code line in the C codes corresponding to an execution unit in the graphic codes can be determined, so as to, in an application scenario of performing further test on the function and the like in the C codes, greatly increase the test efficiency. Moreover, the graphic codes involved in the in some embodiments can be directly executed and the generated C code program can also be directly executed, with their execution processes and execution results being in complete correspondence.

Figure 9:
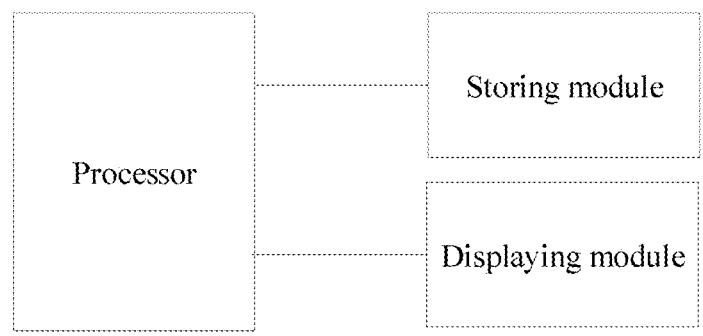
FIG. 9 is a principle block diagram illustrating a conversion apparatus of codes and graphic codes involved in some embodiments of the present disclosure.

As shown in FIG. 9, one or more embodiments further provide a conversion apparatus for text codes and graphic codes, including a processor, configured to execute programs of the conversion method of text codes and graphic codes; a storing module, configured to store the programs of performing the conversion method of text codes and graphic codes in the embodiment; and a displaying module, configured to display a conversion result of the text codes and the graphic codes.

In some embodiments, the conversion apparatus of text codes and graphic codes may also be one of electronic device or computer. The electronic device will be detailed below.

At least one embodiment further provides a conversion method of text codes and graphic codes applied to a vehicle development. The conversion method includes:

converting vehicle graphic codes into text codes, and while generating target codes, inserting configuration information of each execution unit in current vehicle graphic codes into an annotation region of the target codes; and, when converting the target codes back to vehicular graphic codes, extracting the configuration information of the annotation region of the target codes and loading the configuration information to restore vehicular graphic codes.

In a scenario of vehicle development, the specific conversion steps for the text codes and vehicular graphic codes are same as those for the above conversion method of text codes and graphic codes and thus will not be repeated herein.

The conversion method of text codes and graphic codes in a vehicle development scenario is detailed below in combination with specific cases.

Figure 10:
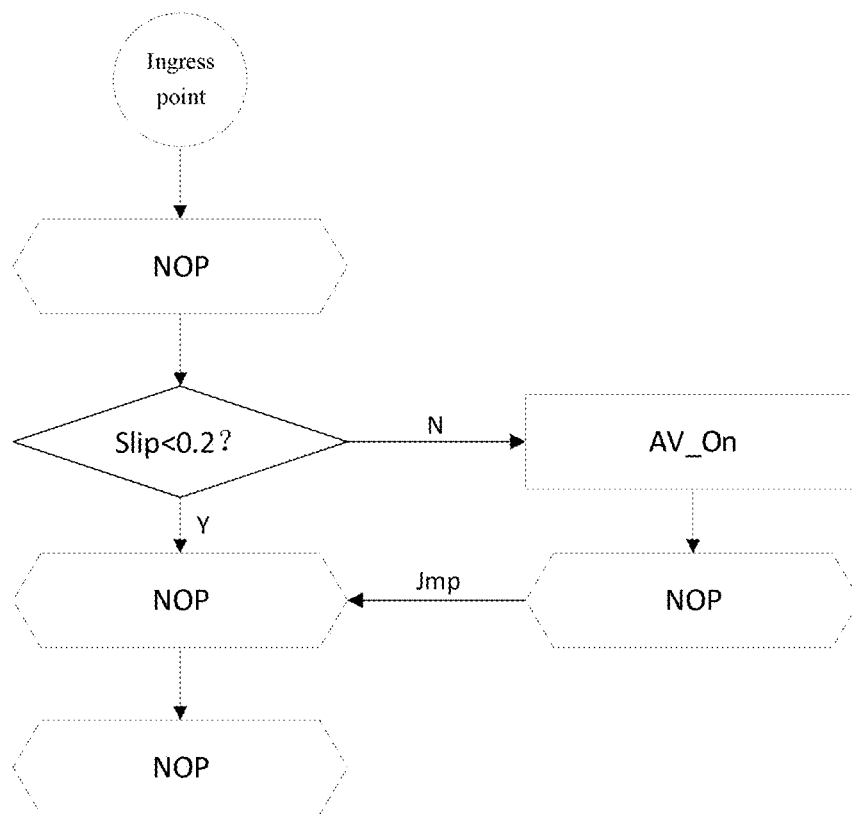
FIG. 10 illustrates a seventh graphic code case involved in some embodiments of the present disclosure.

In an ABS algorithm development process of a vehicle chassis electric control, a logic for controlling a pressure release valve to be opened is taken as an example:

Reference is made to the graphic code fragment shown in FIG. 10.

The logic determines whether a slip of a current wheel is less than 0.2. If the return result is logical false, it indicates the slip of the current wheel is greater than 0.2, and the wheel has a tendency to lock. At this time, it is required to open the pressure release valve to release pressure for the wheel. The flow for generating the C codes from the graphic codes is as follows:

At step S601, the corresponding global unique id is generated for each of the execution units in the graphic codes, where the correspondence between the execution units and the ids is indicated in the Table below:

| Execution unit | id |
|---|---|
| slip<0.2 ? | 3302264560674696091 |
| AV_On | 3428365350600537763 |

At step S602, based on a rule, the C codes are generated line by line from the graphic codes, where there are a total of four lines of codes which are indicated in the Table below:

| Line number | C codes |
|---|---|
| 1 | if (slip <0.2){ |
| 2 | } else { |
| 3 | AV_On( ); |
| 4 | } |

After the codes are generated, an association file f1 in which the code line numbers correspond to the ids is obtained, where there are a total of 4 lines, which are indicated below:

| Line number | id |
|---|---|
| 1 | 3302264560674696091 |
| 2 | empty |
| 3 | 3428365350600537763 |
| 4 | Empty |

At step S603, the graphic codes enable the persistent configuration information of each execution unit to go through base64 encoding. It is assumed that the persistent configuration file f2 of the graphic codes is as follows:

```
[a1]
conf=3302264560674696091;0;3659305742699578;8432990436527128597;342836535
0600537763;0;0;0;0;c2xpcCA8IDAuMiA/;;0;0
[a2]
conf=3428365350600537763;0;3302264560674696091;2570429621957346572;-1;0;1;
0;0;RVZfT24_;;0;0
```

The contents of the association file f1 and the persistent configuration file f2 are base64-encoded, and then inserted in the form of annotation into the annotation region of the generated target C codes. The finally-generated target C codes have the following contents:

```
if (slip <0.2){
} else {
   AV_On( );
}
//MzMwMjI2NDU2MDY3NDY5NjA5MQ0KDQozNDI4MzY1MzUwNjAwNTM3Nz
YzDQoNCg__,W2ExXQ0KY29uZj0zMzAyMjY0NTYwNjc0Njk2MDkxOzA7MzY1OTMw
NTc0MjY5OTU3ODs4NDMyOTkwNDM2NTI3MTI4NTk3OzM0MjgzNjUzNTA2MDA1M
zc3NjM7MDswOzA7MDtjMnhwY0NBOElEQXVNaUEvOzswOzANClthMl0NCmNvbmY
9MzQyODM2NTM1MDYwMDUzNzc2MzswOzMzMDIyNjQ1NjA2NzQ2OTYwOTE7Mj
U3MDQyOTYyMTk1NzM0NjU3MjstMTswOzE7MDswO1JWWmZUMjRfOzswOzANCg
```

At step S604, a user, after compiling the generated target C codes, places the compiled target C codes into a vehicle controller for execution. Thus, the conversion from the vehicle development graphic codes to the C codes is completed.

The application of the positioning information in a vehicle development scenario is detailed below with a logic for controlling a pressure release valve to be opened as an example in an ABS algorithm development process of a vehicle chassis electric control.

Figure 11:
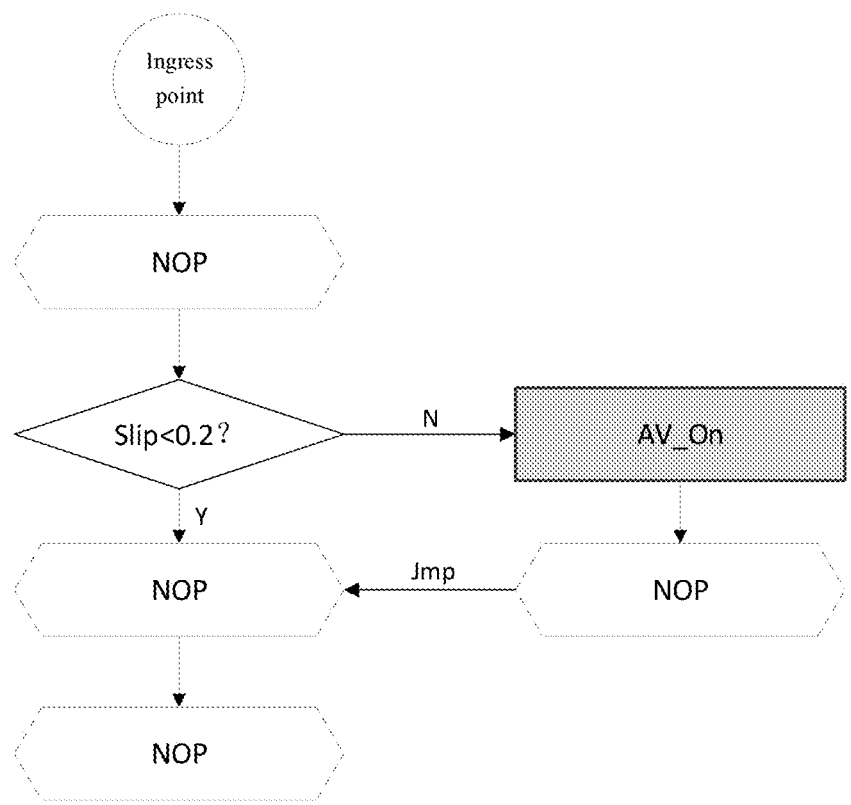
FIG. 11 is a schematic diagram illustrating highlighted AV_On in the seventh graphic code case involved in some embodiments of the present disclosure.

As shown in FIG. 11, when the user finds that a corresponding logic is to be checked for the function for opening the AV valve is disabled, the C code file is firstly loaded by use of the graphic codes and the annotation information in the C code file is read and then base64-decoded to obtain the configuration information and the positioning information of the graphic codes, and then based on the decoded configuration information, the graphic codes are restored. Next, the user clicks the line of codes "AV_On( );" in the window of the C code file loaded by the graphic codes, and the graphic codes can position the execution unit id "3428365350600537763" corresponding to the line number of the line of codes based on the positioning information. Further, the window jumps to the graphic codes and the execution unit is highlighted in the graphic code displaying window to help the user to correct the execution unit, thus significantly increasing the checking convenience and efficiency.

The application of the positioning information in a vehicle test scenario is detailed below with a logic for controlling a pressure release valve to be opened as an example in an ABS algorithm development process of a vehicle chassis electric control.

During an actual vehicle test application, it is required to use the logic of the C codes generated from the graphic codes to perform software in-loop test. Still taking the above logic for controlling the pressure release valve to be opened as a test object, as shown in FIG. 10, the C codes are generated from the graphic code fragment and then further test is to be performed on the function "AV_On" in the C codes to obtain information such as execution time and resource occupation. Thus, it is required to position the corresponding code lines of the C codes by the graphic codes.

The positioning method is as follows: firstly, the user clicks the execution unit "AV_On" in the graphic codes to jump to the corresponding C code line. The graphic codes obtain the execution unit id "3428365350600537763" and read the annotation information in the C code file and obtain the positioning information of the graphic codes, i.e. the correspondence file of code lines and ids, by performing base64 decoding on the annotation information. Then, the graphic codes collect the code lines containing the id in the file and present them to the user in the form of list. The user selects the corresponding item in the list and the corresponding C code line will be positioned and displayed, thus greatly increasing the test efficiency.

The electronic device in the some embodiments will be described below from the perspective of hardware processing.

The embodiments do not limit the specific implementation of the electronic device.

Figure 12:
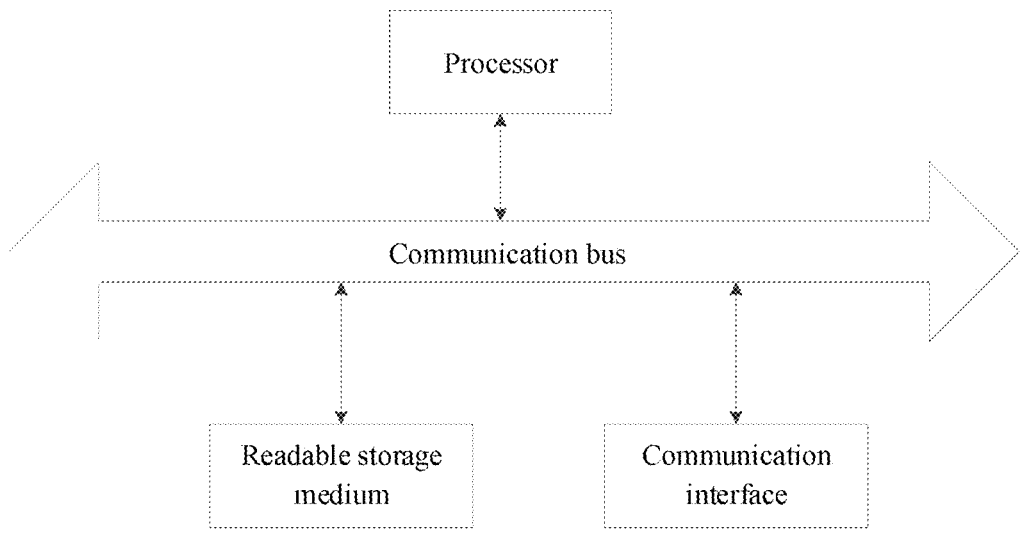
FIG. 12 is a principle block diagram illustrating an electronic device involved in some embodiments of the present disclosure.

As shown in FIG. 12, the present electronic device includes a processor, a readable storage medium, a communication bus and a communication interface. The processor, the readable storage medium and the communication interface communicate with each other via the communication bus. The readable storage medium is configured to store programs of performing the conversion method of text codes and graphic codes, and the programs cause the processor to perform the operations corresponding to the conversion method of text codes and graphic codes.

In other embodiments, a computer device or an industrial personal computer may also be one of the electronic devices.

The structure shown in FIG. 12 does not constitute any limitation to the electronic device and thus may include more or less components than shown in the drawings or combine some components or have different components deployed.

In some embodiments, the communication interface may be RS232, RS485, USB interface or TYPE interface or the like, which may be connected with an external bus adapter. The communication interface may also include wired or wireless network interface. The network interface may optionally include wired interface and/or wireless interface (such as WI-FI interface, Bluetooth interface and the like), which is usually used to establish communication connection between the computer device and other electronic devices.

The storing module, the readable storage medium or the computer readable storage medium include at least one type of memories. The memory includes flash memory, hard disk drive, multimedia card, card type memory (e.g. SD or DX memory or the like), magnetic memory, magnetic disk or compact disk or the like. In some embodiments, the memory may be an internal storage unit in the computer device, for example, a hard disk drive of the computer device. In some other embodiments, the memory may also be an external storage device of the computer device, for example, a plug type hard disk drive, a smart media card (SMC), a secure digital (SD) card, a flash card or the like on the computer device. Furthermore, the memory may include both the internal storage unit and the external storage device in the computer device. The memory may be used to not only store an application software installed on the computer device and various types of data, for example, the codes of the computer programs and the like but also temporarily store data already output or to be output.

In some embodiments, the processor may be a central processing unit (CPU), a controller, a microcontroller, a microprocessor or another data processing chip, which is used to run the program codes in the memory or process the data, for example, execute the computer programs or the like.

In some embodiments, the communication bus may also be an input/output bus, which may be a Peripheral Component Interconnect (PCI) bus, or an Enhanced Industry Standard Architecture (EISA) bus or the like. The bus may include an address bus, a data bus and a control bus and the like.

Optionally, the computer device may also include a user interface, which may include a display, and an input unit, for example, a keyboard. Optionally, the user interface may also include a standard wired interface and wireless interface. Optionally, in some embodiments, the display or the displaying module may be an LED display, a liquid crystal display, a touch liquid crystal display and an Organic Light-Emitting Diode (OLED) touch display and the like. The display or the displaying module may also be appropriately referred to as display screen or display unit for displaying information processed in the computer device as well as a visual user interface.

When executing the above programs, the processor performs the steps in the embodiment of the conversion method of text codes and graphic codes as shown in FIG. 1, for example, the steps S101 to S102 shown in FIG. 1. Alternatively, the processor executes the computer programs to realize the functions of the modules or units in each apparatus embodiment.

In some embodiments, the processor is specifically configured to perform the steps of:
converting the graphic codes into the text codes, and while generating target text codes, inserting configuration information of each execution unit in current graphic codes into an annotation region of the target text codes; and,
when converting the target text codes back to graphic codes, extracting the configuration information of the annotation region of the target text codes and loading the configuration information to restore the graphic codes.

Optionally, as one possible implementation, the processor is further configured to perform the steps of:
inserting the configuration information in the form of text to the annotation region of the target text codes after being subjected to serialization encoding; and,
when converting the target text codes back to the graphic codes, extracting configuration information text of the annotation region for deserialization decoding to obtain the configuration information of each execution unit in the graphic codes, and loading the configuration information to restore the graphic codes.

Optionally, as one possible implementation, the processor is further configured to perform the steps of:
converting sequence execution units in the graphic codes into text codes corresponding to unit actions;
converting branch jump units in the graphic codes into text codes of "if" or "elseif" or "else" structure;
converting nested execution units in the graphic codes into one function executing nested text codes and function-called text codes; and,
converting cyclic units in the graphic codes into one tag, one goto statement and text codes corresponding to the action of the cyclic units.

Optionally, as one possible implementation, the processor is further configured to perform the steps of:
generating persistent configuration information of the graphic codes; and,
inserting the persistent configuration information in the form of text into the annotation region of the target text codes after being subjected to serialization encoding.

Optionally, as one possible implementation, the processor is further configured to perform the steps of:
while generating the target text codes, inserting positioning information of each execution unit in the current graphic codes into corresponding target text code line.

Optionally, as one possible implementation, the processor is further configured to perform the steps of:
when converting the graphic codes into the text codes, establishing a temporary file for temporarily storing the positioning information of each execution unit in the current graphic codes; wherein,
the positioning information is an association file between each execution unit and the corresponding target text code line; and,
the association file, after being subjected to serialization encoding, is inserted in the form of text into the annotation region of the target text codes.

At least one embodiment further provides a computer readable storage medium storing programs for performing the conversion method of text codes and graphic codes. The programs are executed by a processor to perform the specific steps of performing the conversion method of text codes and graphic codes. Reference may be made to the specific descriptions of the conversion method of text codes and graphic codes in the some embodiment and no redundant descriptions will be repeated herein.

Figure 13:
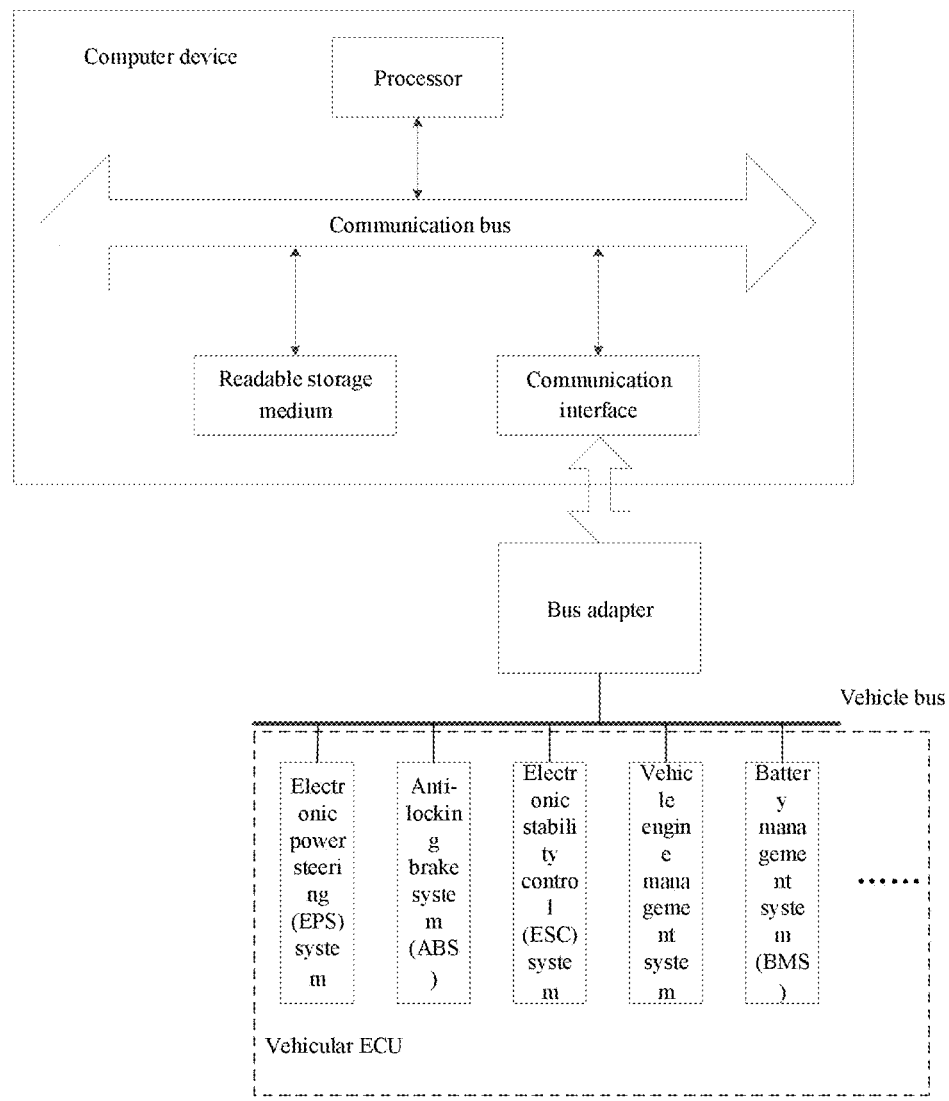
FIG. 13 is a schematic diagram illustrating connection of a vehicular development and debugging system (bus adapter) involved in some embodiments of the present disclosure.
Figures 14, 15:
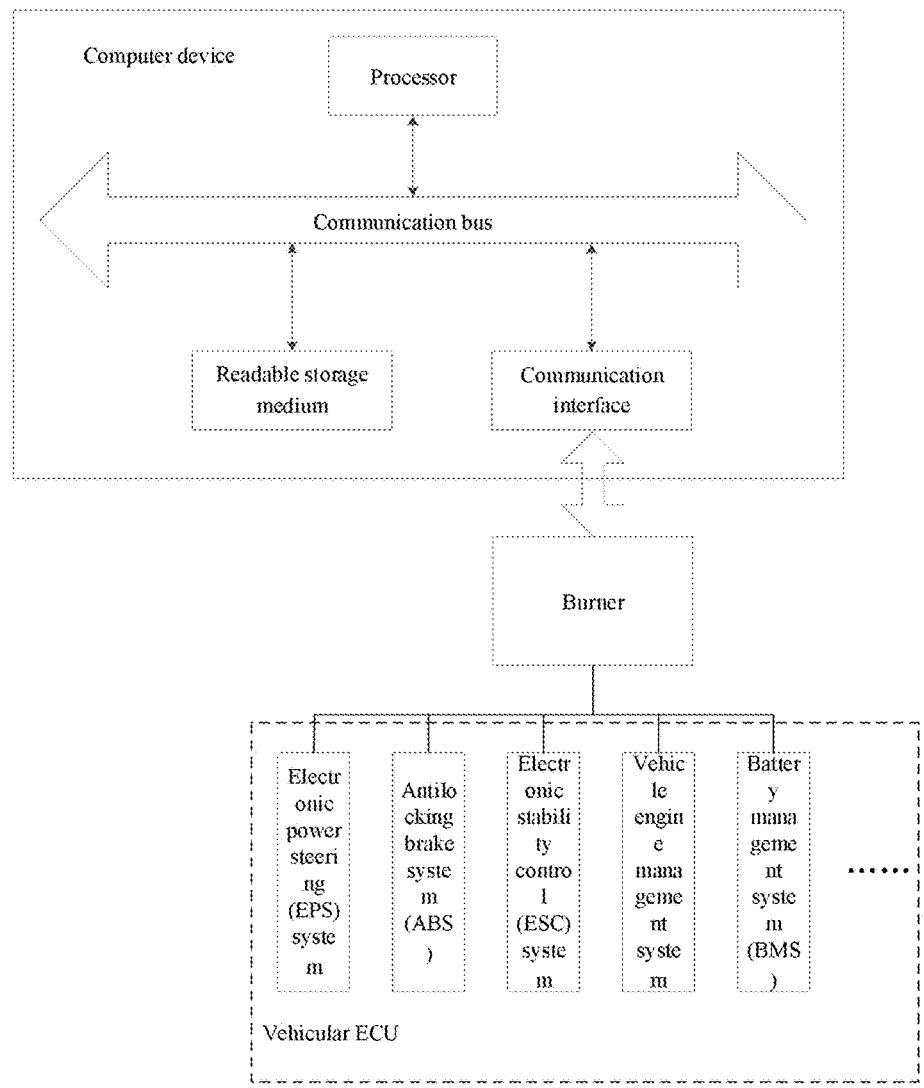
FIG. 14 is a schematic diagram illustrating connection of a vehicular development and debugging system (burner) involved in some embodiments of the present disclosure.
FIG. 15 is a schematic diagram illustrating steps of a vehicular development and debugging method according to some embodiments of the present disclosure.

As shown in FIGS. 13 and 14, one or more embodiments further provide a vehicular development and debugging system, including a computer device, a bus adapter or a burner.

The computer device includes a processor, a readable storage medium, a communication bus and a communication interface; where,
- the readable storage medium is configured to store the programs of performing the conversion method of text codes and graphic codes, and the programs cause the processor to perform operations corresponding to the conversion method of text codes and graphic codes so as to generate the text codes;
- the processor, the readable storage medium and the communication interface communicate with the bus adapter via the communication bus;
- the processor is configured to compile at least one fragment of execution codes in the text codes;
- the bus adapter is configured to write the compiled execution code into a debugging device; or,
- the burner is configured to write the compiled executing code into the debugging device.

As shown in FIG. 15, one or more embodiments further provide a vehicular development and debugging method, which includes:
- at step S201, by a computer device, performing operations corresponding to the conversion method of text codes and graphic codes to generate the text codes; and,
- at step S202, by a bus adapter, writing compiled execution codes into a debugging device, or, by a burner, writing the compiled execution codes into the debugging device. In some embodiments, the computer device corresponds to the above electronic device, and no redundant descriptions are made herein.

The processor is configured to compile at least one fragment of execution codes in the text codes; in some embodiments, the compilation of the text codes can be performed by using a cross compiler.

In some embodiments, the configuration information, after being subjected to serialization encoding, is inserted in the form of text into an annotation region of target text codes; and, when converting the target text codes back to graphic codes, a graphic program extracts the configuration information text of the annotation region for deserialization operation to obtain the configuration information of each execution unit in the graphic codes and the configuration information is loaded to restore the graphic codes.

In some embodiments, converting the graphic codes into the text codes includes: converting sequence execution units in the graphic codes into text codes corresponding to unit actions; converting branch jump units in the graphic codes into text codes of "if" or "else if" or "else" structure; converting nested execution units in the graphic codes into one function executing nested text codes and function-called text codes; and, converting cyclic units in the graphic codes into one tag, one goto statement and text codes corresponding to the action of the cyclic units.

In some embodiments, inserting the configuration information into the annotation region of the target text codes includes: generating persistent configuration information of the graphic codes; and, inserting the persistent configuration information in the form of text into the annotation region of the target text codes after being subjected to serialization encoding.

In some embodiments, while generating the target text codes, positioning information of each execution unit in the current graphic codes is inserted into corresponding target text code line.

In some embodiments, when the graphic codes are converted into the text codes, a temporary file is established for temporarily storing the positioning information of each execution unit in the current graphic codes; where the positioning information is an association file between each execution unit and the corresponding target text code line; and, the association file, after being subjected to serialization encoding, is inserted in the form of text into the annotation region of the target text codes.

In some embodiments, the bus adapter may be a CAN bus adapter, a CANFD bus adapter, a FastLIN bus adapter, a LIN bus adapter, an Ethernet bus adapter, a FlexRay bus adapter or may be one to multiple or multiple to multiple, which is not limited for the specific implementation in some embodiments. In some embodiments, the compiled execution codes may be written by communicating with the debugging device based on UDS, XCP or CCP protocol.

In some embodiments, the burner may also refer to a programmer.

In some embodiments, The debugging device in the vehicle field may specifically be a vehicular ECU and its relevant system, for example, include but not limited to an electronic power steering (EPS) system, an anti-locking brake system (ABS), an electronic stability control (ESC) system, an vehicle engine management system, a battery management system (BMS) and the like, which can be connected to the computer device via the bus to receive and run the compiled execution codes.

In some embodiments, A computer readable storage medium, storing computer readable instructions, wherein the computer readable instructions are executed by at least one processor to perform the method:
- converting the graphic codes into the text codes, and while generating target text codes, inserting configuration information of each execution unit currently in the graphic codes into an annotation region of the target text codes; and
- when converting the target text codes back to the graphic codes, extracting, by a graphic program, the configuration information of the annotation region of the target text codes and loading the configuration information to restore the graphic codes.

In some embodiments, A computer program product, comprising a computer readable storage medium on which computer readable program codes are stored, wherein the computer readable program codes comprise instructions, which cause at least one processor (one or more computer devices) to perform the following operations:
- converting the graphic codes into the text codes, and while generating target text codes, inserting configuration information of each execution unit currently in the graphic codes into an annotation region of the target text codes; and
- when converting the target text codes back to the graphic codes, extracting, by a graphic program, the configuration information of the annotation region of the target text codes and loading the configuration information to restore the graphic codes.

In the several embodiments provided by the present disclosure, it should be understood that the disclosed device and method can be implemented another way. The above device embodiments are merely illustrative, for example, the flowcharts or block diagrams in the drawings show possible system architectures, functions and operations of the device, method, and computer program product in the several embodiments provided by the present disclosure. Thus, each block in the flowcharts or block diagrams may represent one module, one program fragment or one part of codes. The module, the program fragment or the part of codes includes one or more executable instructions for implementing the specified logic functions. It should be noted that in some alternative embodiments, the functions indicated in the blocks may also be performed in a sequence different from that indicated in the drawings. For example, two continuous blocks can be actually performed basically in parallel, and sometimes may be performed in a reverse sequence, which is dependent on the functions involved. It is further noted that each block in the block diagrams and/or flowcharts and the combinations of the blocks in the block diagrams and/or flowcharts may be implemented by a dedicated hardware-based system for executing specified functions or actions, or by combination of dedicated hardware and computer instructions.

Furthermore, the functional modules in the embodiments of the present disclosure can be integrated into one independent part, or exist as separate modules or two or more of the modules are integrated into one independent part.

The functions, when implemented by software function modules and sold or used as independent products, can be stored in one computer readable storage medium. Based on such understanding, the essence of technical solutions of the present disclosure, or a part contributing to the prior arts or a part of the technical solutions can be embodied in the form of software product. The computer software product is stored in one storage medium which includes several instructions to enable one computer device (for example, a personal computer, a server, or a network device or the like) to perform all or part of the steps of the method of each of the embodiments of the present disclosure.

Enlightened by the ideal embodiments of the present disclosure, relevant workers can, based on the contents of the specification, make various changes and modifications within the scope of protection of the technical idea of the present disclosure. The technical scope of the present disclosure is not limited to the contents of the specification but to the technical scope claimed by the claims.

One or more embodiments of the present disclosure provide a computer program product, including a computer program or instruction, where the computer program or instruction is executed on a computer to cause the computer to perform any one of the above conversion methods of text codes and graphic codes.

The invention claimed is:

1. A conversion method of text codes and graphic codes, comprising:
converting the graphic codes into the text codes, and while generating target text codes, inserting configuration information of each execution unit currently in the graphic codes into an annotation region of the target text codes; and
when converting the target text codes back to the graphic codes, extracting, by a graphic program, the configuration information of the annotation region of the target text codes and loading the configuration information to restore the graphic codes.

2. The conversion method of claim 1, further comprising:
inserting the configuration information in the form of text to the annotation region of the target text codes after being subjected to serialization encoding; and
when converting the target text codes back to the graphic codes, extracting, by the graphic program, configuration information text of the annotation region for deserialization decoding to obtain the configuration information of each execution unit in the graphic codes, and loading the configuration information to restore the graphic codes.

3. The conversion method of claim 2, wherein,
the inserting of the configuration information into the annotation region of the target text codes further comprises:
generating persistent configuration information of the graphic codes; and
inserting the persistent configuration information in the form of text into the annotation region of the target text codes after being subjected to serialization encoding.

4. The conversion method of claim 3, further comprising:
while generating the target text codes, inserting positioning information of each execution unit in the current graphic codes into a corresponding target text code line.

5. The conversion method of claim 3, further comprising:
when converting the graphic codes into the text codes, establishing a temporary file for temporarily storing the positioning information of each execution unit in the current graphic codes; wherein,
the positioning information is an association file between each execution unit and the corresponding target text code line; and
the association file, after being subjected to serialization encoding, is inserted in the form of text into the annotation region of the target text codes.

6. The conversion method of claim 1, wherein,
the converting of the graphic codes into the text codes further comprises:
converting sequence execution units in the graphic codes into text codes corresponding to unit actions;
converting branch jump units in the graphic codes into text codes of "if" or "else if" or "else" structure;
converting nested execution units in the graphic codes into one function executing nested text codes and function-called text codes; and
converting cyclic units in the graphic codes into one tag, one goto statement, and text codes corresponding to the action of the cyclic units.

7. A conversion apparatus for text codes and graphic codes, comprising:
a processor, configured to execute programs of the conversion method of text codes and graphic codes according to claim 1;
a storing module, configured to store the programs; and
a displaying module, configured to display a conversion result of the text codes and the graphic codes.

8. A computer readable storage medium, storing computer readable instructions, wherein the computer readable instructions are executed by at least one processor to perform the method according to claim 1.

9. An electronic device, comprising: a processor, a readable storage medium, a communication bus, and a communication interface, wherein the processor, the readable storage medium and the communication interface communicate with each other via the communication bus; and
the readable storage medium is configured to store the programs of performing the conversion method of text codes and graphic codes according to claim 1, and the programs cause the processor to perform operations corresponding to the conversion method of text codes and graphic codes.

10. A conversion method of text codes and graphic codes applied to a vehicle development, comprising:
- converting vehicular graphic codes into text codes, and while generating target text codes, inserting configuration information of each execution unit in current vehicular graphic codes into an annotation region of the target text codes; and
- when converting the target text codes back to vehicular graphic codes, extracting, by a vehicular graphic program, the configuration information of the annotation region of the target text codes and loading the configuration information to restore vehicular graphic codes.

11. The conversion method of claim 10, further comprising:
- inserting the configuration information in the form of text to the annotation region of the target text codes after being subjected to serialization encoding; and
- when converting the target text codes back to vehicular graphic codes, extracting, by the vehicular graphic program, configuration information text of the annotation region for deserialization decoding to obtain the configuration information of each execution unit in vehicular graphic codes, and loading the configuration information to restore vehicular graphic codes.

12. The conversion method of claim 11, wherein, the inserting of the configuration information into the annotation region of the target text codes further comprises:
- generating persistent configuration information of vehicular graphic codes; and
- inserting the persistent configuration information in the form of text into the annotation region of the target text codes after being subjected to serialization encoding.

13. The conversion method of claim 12, further comprising:
- while generating the target text codes, inserting positioning information of each execution unit in the current vehicular graphic codes into a corresponding target text code line.

14. The conversion method of claim 12, further comprising:
- when converting vehicular graphic codes into the text codes, establishing a temporary file for temporarily storing the positioning information of each execution unit in the current vehicular graphic codes; wherein,
- the positioning information is an association file between each execution unit and the corresponding target text code line; and
- the association file, after being subjected to serialization encoding, is inserted in the form of text into the annotation region of the target text codes.

15. The conversion method of claim 10, wherein,
the converting of vehicular graphic codes into the text codes further comprises:
- converting sequence execution units in vehicular graphic codes into text codes corresponding to unit actions;
- converting branch jump units in vehicular graphic codes into text codes of "if" or "else if" or "else" structure;
- converting nested execution units in vehicular graphic codes into one function executing nested text codes and function-called text codes; and
- converting cyclic units in vehicular graphic codes into one tag, one goto statement and text codes corresponding to the action of the cyclic units.

* * * * *